United States Patent [19]

Labrie

[11] Patent Number: 4,666,885

[45] Date of Patent: May 19, 1987

[54] COMBINATION THERAPY FOR TREATMENT OF FEMALE BREAST CANCER

[76] Inventor: Fernand Labrie, 2735 boul Liegeois, St-Foy, Quebec, G1W 1Z9, Canada

[21] Appl. No.: 699,702

[22] Filed: Feb. 8, 1985

[51] Int. Cl.$^4$ .............................................. A61K 37/24
[52] U.S. Cl. ................................................ 514/15
[58] Field of Search .................... 260/112.5 R; 514/15

[56] References Cited

U.S. PATENT DOCUMENTS

| | | | |
|---|---|---|---|
| 4,024,248 | 5/1977 | König et al. | 424/177 |
| 4,071,622 | 1/1978 | Johnson et al. | 424/177 |
| 4,094,994 | 6/1979 | Schönenberger et al. | 424/177 |
| 4,097,578 | 6/1978 | Perronnet et al. | 424/273 R |
| 4,100,274 | 7/1978 | Dutta et al. | 424/177 |
| 4,118,483 | 10/1978 | König et al. | 424/177 |
| 4,239,776 | 12/1980 | Glen et al. | 424/304 |
| 4,329,364 | 5/1982 | Neri et al. | 424/324 |
| 4,386,080 | 5/1983 | Crowley et al. | 424/209 |
| 4,472,382 | 9/1984 | Labrie et al. | 424/177 |
| 4,481,190 | 11/1984 | Nestor et al. | 424/177 |

FOREIGN PATENT DOCUMENTS

| | | |
|---|---|---|
| 637389 | 3/1964 | Belgium . |
| 58481 | 8/1982 | European Pat. Off. . |
| 78158 | 5/1983 | European Pat. Off. . |

OTHER PUBLICATIONS

Cancer Research 42, 4788–4791 (1982).
J. Steroid Biochem., vol. 19, No. 1, pp. 999–1007 (1983).
J. of Steroid Biochem., vol. 14, pp. 819–822 (1981).
Nature, vol. 313 (1985), pp. 231–233.
Cancer Treatment Reports, vol. 68 (No. 1), pp. 281–289 (1984), A. V. Schally et al.
Proc. Natl. Acad. Sci. USA, vol. 80, pp. 1459–1462 (1983), T. W. Redding and A. V. Schally.
"LH-RH Analogs in the Treatment of Human Breast Cancer", H. A. Harvey et al., in *LHRH and Its Analogs-A New Class of Contraceptive and Therapewtic Agents*, pp. 329–335, (B. H. Vickery et al. etc.) MTP Press Lancaster VIC/1192.
Doll, R., et al., Cancer Incidence in Five Continents, II Springer-Verlag, (UICC Publications, New York) 1970.
Wang, D. Y. et al., Europ. J. Cancer (1976) vol. 12, pp. 951–958.
Adams, J. B., Cancer (1977), vol. 40, pp. 325–333.
Wong, D. Y., et al., Europ. J. Cancer (1975), vol. 11, pp. 873–879.
Secreto, G., et al., Europ. J. Cancer. Clin. Oncol. (1983), vol. 19, pp. 5–10.
F. Labrie et al., "Inhibition of Testicular and Ovarian Functions by LHRH Agonists," In: Bioregulators of Reproduction, (1982) Academic Press, pp. 305–341.
Meldrum, D. R., et al., J. Clin. Endocrinol. Metab., (1982), vol. 54, pp. 1081–1083.
Nicholson, R. I., et al. Reviews in Endocrine-Related Cancer (1984), Nicholson, R. I. and Griffins, K., eds).
Klijn, J. G. and De Jong, F. H., The Lancet (1982), pp. 1213–1216.
J. Steroid Biochem., vol. 20 (No. 6B) 1381 (1984), J. G. M. Klijn et al.
J. Med. Chem., vol. 21 1018–1024 (1978), A. S. Dutta et al.
Biochem. Biophy. Res. Commun., vol. 100, pp. 915–920 (1981) J. Erchegg, et al.
Endocrinology, vol. 110, pp. 1445–1447 (1982); D. H. Coy et al.
J. Steroid. Biochem., vol. 20 (No. 6B), 1366 (1984); J. J. Nestor et al.
J. Steroid Biochem., vol. 20, (No. 6B) 1365 (1984); J. Rivier et al.
J. Steroid Biochem., vol. 20 (No. 6B) p. 1369 (1984); A. Corbin et al.
LH-RH and Its Analogs (B. H. Vickery et al. Editors), pp. 3–10, J. J. Nestor.
LH-RH and Its Analogs (B. H. Vickery et al. Editors), pp. 11–22, J. Rivier et al.
LH-RH and Its Analogs (B. H. Vickery et al. Editors) pp. 23–33, J. J. Nestor et al.
"Solid Phase Peptide Synthesis", Stewart et al. Freman and Co., San Francisco, CA. (1969), pp. 1–26.
J. Med. Chem., vol. 19, pp. 423–425 (1976) D. H. Coy et al.
Trams, G. and Maass, S. H., Cancer Res. (1977), vol. 37, pp. 258–261.
Flax, H. et al., The Lancet (1973) pp. 1204–1207.
Wagner, R. K. and Jungblut, P. W., Acta Endocrinologica (1976), vol. 82, pp. 105–120.
Matsumoto, K. et al. Hormonal Regulators of Mammary Tumors (1984), B. S. Leung ed.; Eden Press, Inc. (1984), pp. 216–244.
Lancet, 1, 1213–1216 (1982), J. G. M. Klijn et al., (The Lancet, May 29, 1982).
Cancer, vol. 50, 1708–1712 (1982), A. V. Buzdar et al.
Lancet, 1204–1207 (1973), H. Flax et al. (The Lancet; Jun. 2, 1973).

(List continued on next page.)

*Primary Examiner*—Delbert R. Phillips
*Attorney, Agent, or Firm*—Thomas D. Hoffman; Gerald S. Rosen

[57] ABSTRACT

A method of treatment of breast cancer in susceptible animals whose ovarian hormonal secretions are blocked by surgical or chemical means, e.g., by use of an LH-RH agonist, e.g., [D-Trp$^6$, des-Gly-NH$_2^{10}$]LH-RH ethylamide with a therapy comprising administering an antiandrogen, e.g., flutamide and an optionally, an inhibitor of adrenal sex steroid biosynthesis e.g., aminoglutethimide, pharmaceutical compositions useful for such treatment and two, four and five component pharmaceutical kits containing such compositions are disclosed.

34 Claims, No Drawings

OTHER PUBLICATIONS

The Prostate, vol. 4, 579–594 (1983), F. Labrie et al.
Cancer Treatment Review, vol. 5, 131–141 (1978), H. Movridsen et al.
J. L. Hayward et al., Cancer (Mar. 1977), vol. 39, pp. 1289–1294.
C. Huggins et al., Ann. Surg. (1945), vol. 122, pp. 1031–1041.
C. Huggins et al., JAMA (1951), vol. 147, pp. 101-1-6.
A. A. Fracchia et al., Surg. Gynecol. Obstet (1967), vol. 125, pp. 747–756.
H. S. Harris et al., Cancer (1969), vol. 24, pp. 145–151.
Brown, P. W., et al., Arch. Surg. (1975), vol. 110, pp. 77–81.
Silverstein, M. J. et al., Surgery, (1975), vol. 77, pp. 825–832.
Smith, I. E., et al., Brit. Med. J. (1981), vol. 283, pp. 1432–1434.
Buzdar, A. V. et al., Cancer (1982), vol. 50, pp. 1708–1712.
Santen, R. J., et al., New. Engl. J. Med., (1981), vol. 305, pp. 545–551.
Seymour–Munn, K. and Adams, J., Endocrinology (1983), vol. 112, pp. 486–491.
Reed, M. J. et al., Cancer Research (1983), vol. 43, pp. 3940–3943.

COMBINATION THERAPY FOR TREATMENT OF FEMALE BREAST CANCER

CROSS-REFERENCE TO RELATED APPLICATION

This application is related to U.S. patent application Ser. No. 636,883, filed on August 2, 1984.

BACKGROUND OF THE INVENTION

This invention relates to a method of treatment of breast cancer in susceptible warm-blooded female animals including humans using a therapy comprising administering an antiandrogen to such animals after the hormone output of their ovaries has been blocked by surgical or chemical means. The invention also includes pharmaceutical compositions useful for such treatment and pharmaceutical kits containing such compositions. In its most preferred aspect, this invention relates to treatment of breast cancer in warm-blooded animals by parenterally administering an LH—RH agonist or LH—RH antagonist, in association with orally administering an antiandrogen and orally administering an antiestrogen and orally administering an inhibitor of sex steroid biosynthesis.

While various investigators have been studying hormone-dependent breast and prostate cancer, none have proposed the combination therapy of this invention.

A. V. Schally et al., Cancer Treatment Reports, 68, (No. 1) 281–289 (1984), summarize the results of animal and clinical studies on growth inhibition of hormone-dependent mammary and prostate tumors by use of analogues of luteinizing hormone-releasing hormones, the so-called LH—RH agonists and suggest that LH—RH analogs and/or antagonists may have potential for treating breast cancer.

T. W. Redding and A. V. Schally, Pro. Natl. Acad. Sci. USA, 80, 1459–1462 (1983), disclose reduction of estrogen-dependent mammary tumors in rats and mice by use of an LH—RH agonist, [D-Trp$^6$]LH—RH or of two specific antagonists.

In U.S. Pat. No. 4,071,622, it is disclosed that use of certain LH—RH agonists causes regression of DMBA-induced mammary carcinoma in rats.

In U.S. Pat. No. 4,472,382, it is disclosed that certain LH—RH agonists alone may be useful in the treatment of prostate adenocarcinoma and hormone-dependent mammary tumors. While the use of certain LH—RH agonists and an antiandrogen are disclosed for treatment of prostate adenocarcinoma and benign prostate hypertrophia, there is no disclosure or suggestion of the present invention.

Some clinical improvement in premenopausal women with breast cancer by use of the two LH—RH agonists, Buserelin and Leuprolide, is also reported by H. A. Harvey et al. "LH—RH analogs in the treatmemt of human breast cancer", *LH—RH and Its Analogs—A New Class of Contraceptive and Therapeutic Agents* (B. H. Vickery and J. J. Nestor, Jr., and E. S. E. Hafez, eds) Lancester, MTP Press, (1984) and by J. G. M. Klijn et al. "Treatment with luteinizing hormone releasing hormone analogue (Buserelin) in premenopausal patients with metastatic breast cancer", Lancet, 1, 1213–1216 (1982).

Treatment of advanced breast cancer with aminoglutethimide after therapy with the antiestrogen, Tamoxifen is disclosed by A. V. Buzdar et al., Cancer, 50, 1708–1712 (1982).

H. Flax et al., Lancet, 1204–1207, (1973), suggest some women's breast cancers are androgen-dependent.

F. Labrie et al., The Prostate, 4, 579–594 (1983), disclose that use of a combination therapy of an LH—RH agonist (Buserelin) and an antiandrogen (Anandron) to treat advanced prostate cancer in previously untreated patients effects simultaneous elimination of androgens of both testicular and adrenal origin.

F. Labrie et al., J. Steroid Biochem., 19, 99–1007 (1983), disclose the treatment of prostate cancer by the combined administration of an LH—RH agonist and an antiandrogen. Labrie et al. disclose animal and clinical data in support of the proposition that the combined LH—RH/antiandrogen treatment neutralizes the stimulatory influence of all androgens on the development and growth of androgen-dependent prostatic cancer.

In U.S. Pat. No. 4,094,994, it is disclosed that the use of antiestrogens such as meso-3,4-bis(3'-hydroxyphenyl)hexane inhibits MCF7 human breast tumor cells. In fact, the inhibitory activity of the antiestrogen was antagonized by estradiol.

H. Mouridsen et al,. Cancer Treatment Review 5, 131–141, (1978), disclose that Tamoxifen, an antiestrogen is effective in remission of advanced breast cancer in about 30% of the patients treated.

J. G. M. Klijn et al., (J. Steroid Biochem, Vol. 20 (No. 6B), 1381 (1984), disclose the combined use of the antiestrogen, Tamoxifen, and the LH—RH agonist, Buserelin, for treatment of breast cancer is known, but objective remission of such cancers remains low (35%).

BRIEF DESCRIPTION OF THE INVENTION

In its broadest aspect, the invention provides a method of treating breast cancer in a warm-blooded female animal in need of such treatment which comprises blocking the ovarian hormonal secretions of said animal by surgical or chemical means and in association therewith, administering to said animal a therapeutically effective amount of an antiandrogen or a pharmaceutical composition thereof. In one aspect, the invention provides a method of treating breast cancer in a castrated warm-blooded female animal, i.e., such a female animal whose ovaries were previously blocked by surgical or chemical means from secreting estrogen, which comprises administering to such a female in need of such treatment an antiandrogen in association with at least one inhibitor of sex steroid biosynthesis and, optionally, an antiestrogen, or pharmaceutical compositions thereof, in amounts sufficient to treat breast cancer. By completely blocking sex steroids (androgens and estrogens) production and/or action, the present invention provides a method of inhibiting the growth of hormone-sensitive breast tumors in warm-blooded animals having such tumors.

In female mammals, the ovaries may be surgically removed (oophorectomy) but preferably the secretion of estrogens from the ovaries is blocked by chemical castration by administering an effective amount of an LH—RH agonist or antagonist. Thus, in a preferred aspect, the present invention provides a method of treating breast cancer in a warm-blooded female animal, which comprising administering to such a female in need of such treatment an LH—RH agonist or antagonist, in association with an antiandrogen and at least one inhibitor of sex steroid biosynthesis, or pharmaceutical compositions thereof, in amounts sufficient to treat breast cancer.

In its preferred aspect, the LH—RH agonist is administered parenterally (subcutaneously or intramuscularly) and, in association therewith, the antiandrogen and the inhibitor of sex steroid biosynthesis are each administered orally. The invention also provides kits or single packages combining the two, four and five separate preferred pharmaceutical compositions; the two component kit provides the antiandrogen oral pharmaceutical composition and the LH—RH agonist or LH—RH antagonist parenteral composition; the four component kit provides the LH—RH agonist or LH—RH antagonist parenteral pharmaceutical composition, the antiandrogen oral pharmaceutical composition and, the sex steroid biosynthesis inhibitor oral pharmaceutical composition and the hydrocortisone oral pharmaceutical composition and the five component kit provides the LH—RH agonist or LH—RH antagonist parenteral pharmaceutical composition, the antiandrogen oral pharmaceutical composition, the antiestrogen oral pharmaceutical composition, the sex steroid biosynthesis inhibitor oral composition and the hydrocortisone oral pharmaceutical composition.

Thus, this invention provides a novel method for effective treatment of breast cancer, in the absence of an antiestrogen. In addition, the amounts of antiestrogen required when administered in association with this combined therapy are lower than normally used in prior art methods, e.g., J. G. M. Klijn et al., J. Steroid Biochem. 20 (No. 6B) 1381 (1984), to treat breast cancer, and thus, the harmful effects of relatively large doses of antiestrogen are minimized.

DETAILED DESCRIPTION OF THE INVENTION

In one preferred aspect, the present invention provides an effective method of treating breast cancer in warm-blooded female animals in need of such treatment by administering an LH—RH agonist or antagonist, in association with an antiandrogen and an inhibitor of sex steroid biosynthesis or pharmaceutical compositions thereof in amounts sufficient to inhibit breast tumor growth. These active compounds can be administered together or in any order as discussed hereinafter. To assist in determining the effect of the treatment, blood plasma concentrations of the sex steroids of adrenal origin, i.e., adrenal androgens and estrogens, and tumor size are measured. Lowered concentrations of sex steroids and reduction in tumor size are indicative of successful treatment, e.g. inhibition of tumor growth using active compounds described herein in accordance with the present invention. The concentrations of adrenal androgens and estrogens such as dehydroepiandrosterone (DHEA), DHEA-sulfate (DHEAS), androst-5-ene-$3\beta$, $17\beta$-diol ($\Delta^5$-diol) and, the ovarian estrogen, $17\beta$-estradiol ($E_2$) are measured by standard methods well known to those skilled in the art, see for example F. Labrie et al., The Prostate, 4, 579–594 (1983).

The change in tumor size is measured by standard physical methods well known to those skilled in the art, e.g., bone scan, chest X-ray, skeletal survey, ultrasonography of the liver and liver scan (if needed), CAT-scan and physical examination.

While a LH—RH agonist or a LH—RH antagonist may be used in one preferred aspect of the present invention, the use of a LH—RH agonist is more preferred.

By the term "LH—RH agonist" is meant synthetic analogues of the natural luteinizing hormone-releasing hormone (LH—RH), a decapeptide of the structure: L-pyroglutamyl-L-histidyl-L-tryptophyl-L-seryl-L-tyrosyl-glycyl-L-leucyl-L-arginyl-L-prolylglycyl-NH$_2$ Typical suitable LH—RH agonists include nonapeptides and decapeptides represented by the formula: L-pyroglutamyl-L-histidyl-L-tryptophyl-L-seryl-L-tyrosyl-X-Y-L-arginyl-L-prolyl-Z
wherein X is D-tryptophyl, D-leucyl, D-alanyl, iminobenzyl-D-histidyl, 3-(2-naphthyl)-D-alanyl, O-tert-butyl-D-seryl, D-tyrosyl, D-lysyl, D-phenylalanyl or N-methyl-D-alanyl and Y is L-leucyl, D-leucyl, N$^\alpha$-methyl-D-leucyl or N$^\alpha$-methyl-L-leucyl or D-alanyl and wherein Z is glycyl-NHR$_1$ or NHR$_1$ wherein R$_1$ is H, lower alkyl or haloloweralkyl. Lower alkyl includes straight or branched chain alkyls having 1 to 6 carbon atoms, e.g., methyl, ethyl, propyl, pentyl or hexyls, iso-butyl, neopentyl and the like. Haloloweralkyl includes straight and branched chain alkyls of 1 to 6 carbon atoms having a halogen substituent, e.g., —CF$_3$,—CH$_2$CF$_3$,—CF$_2$CH$_3$. Halogen means F, Cl, Br, with F being preferred.

Preferred nonapeptides wherein Y is L-leucyl and X is an optically active D-form of selected amino acids and Z is NHC$_2$H$_5$ are [D-Trp$^6$, des-gly-NH$_2^{10}$]-LH—RH ethylamide (X=D-Trp$^6$); [D-Ser-(t-BuO)$^6$, des-gly-NH$_2^{10}$]-LH—RH ethylamide [X=D-Ser(t-BuO$^6$)]; [D-Leu$^6$, des-gly-NH$_2^{10}$]-LH—RH ethylamide (X=D-Leu$^6$); [D-His(Bzl)$^6$, des-gly-NH$_2^{10}$]-LH—RH ethylamide (X=iminobenzyl-D-His$^6$) and [D-Ala$^6$, des-gly-NH$_2^{10}$]-LH—RH ethylamide (X=D-Ala$^6$).

Preferred decapeptides include [D-Trp$^6$]-LH—RH wherein X=D-Trp, Y=L-leucyl, Z=glycyl-NH$_2$, [D-Phe$^6$]-LH—RH wherein X=D-phenylalanyl, Y=L-leucyl and Z=glycyl-HN$_2$) or [D-Nal(2)$^6$]-LH—RH which is [(3-(2-naphthyl)-D-Ala$^6$]-LH—RH wherein X=3-(2-naphthyl)-D-alanyl, Y=L-leucyl and Z=glycyl-NH$_2$.

Other LH—RH agonists useful within the scope of this invention are the α-aza analogues of the natural LH—RH, especially, [D-Phe$^6$, Azgly$^{10}$]-LH—RH, [D-Tyr(Me)$^6$, Azgly$^{10}$]-LH—RH, and [D-Ser-(t-BuO)$^6$, Azgly$^{10}$]-LH—RH disclosed by A. S. Dutta et al. in J. Med. Chem., 21, 1018 (1978) and U.S. Pat. No. 4,100,274 as well as those disclosed in U.S. Pat. Nos. 4,024,248 and 4,118,483.

Typical suitable LH—RH antagonists include [N-Ac-D-p-Cl-Phe$^{1,2}$, D-Phe$^3$, D-Arg$^6$, D-Ala$^{10}$]-LH—RH disclosed by J. Ercheggi et al., Biochem. Biophys. Res. Commun. 100, 915–920, (1981); [N-Ac-D-p-Cl-Phe$^{1,2}$, D-Trp$^3$, D-Arg$^6$, D-Ala$^{10}$]LH—RH disclosed by D. H. Coy et al., Endocrinology, 110: 1445–1447, (1982); [N-Ac-D-(3-(2-naphthyl)-Ala)$^1$, D-p-Cl-Phe$^2$, D-Trp$^3$, D-hArg(Et$_2$)$^6$, D-Ala$^{10}$]-LH—RH and [N-Ac-Pro$^1$, D-p-F-Phe$^2$, D-(3-(2-naphthyl)Ala$^{3,6}$]-LH—RH disclosed by J. J. Nestor et al. J. Steroid Biochem., 20 (No. 6B), 1366 (1984); the nona- and decapeptide LH—RH analogs useful as LH—RH antagonists disclosed in U.S. Pat. No. 4,481,190 (J. J. Nestor et al.); analogs of the highly constrained cyclic antagonist, cycle [$\Delta^3$ Pro$^1$, D-p-Cl-Phe$^2$, D-Trp$^{3,6}$, N-Me-Leu$^7$,$\beta$-Ala$^{10}$]-LH—RH disclosed by J. Rivier, J. Steroid Biochem., 20, (No. 6B), 1365 (1984), and [N-Ac-D-(3-(2-naphthyl)-Ala)$^1$, D-p-F-Phe$^2$, D-Trp$^3$, D-Arg$^6$]-LH—RH disclosed by A. Corbin et al., J. Steroid Biochem. 20 (No. 6B) 1369 (1984).

Other LH—RH agonist and antagonist analogs are disclosed in *LH—RH and Its Analogs* (B. H. Vickery et al.) at pages 3-10 (J. J. Nestor) and pages 11-22 (J. Rivier et al.) and pages 23-33 (J. J. Nestor et al.).

The LH—RH agonists and antagonists useful in this invention may conveniently be prepared by the method described by Stewart et al. in "Solid Phase Peptide Synthesis" (published in 1969 by Freeman & Co., San Francisco, page 1) but solution phase synthesis may also be used.

The nona- and decapeptides used in this invention are conveniently assembled on a solid resin support, such as 1% cross-linked Pro-Merrifield resin by use of an automatic peptide synthesizer. Typically, side-chain protecting groups, well known to those in the peptide arts, are used during the dicyclohexylcarbodiimidecataylzed coupling of a tert-butyloxycarbonylamino acid to the growing peptide attached to a benzhydrylamine resin. The tert-butyloxycarbonyl protecting groups are removed at each stage with trifluoroacetic acid. The nona- or decapeptide is cleaved from the resin and deprotected by use of HF. The crude peptide is purified by the usual techniques, e.g., gel filtration and partition chromatography and optionally lyophilization. See also D. H. Coy et al., J. Med. Chem. 19, pages 423-425, (1976).

Typical suitable antiandrogens include non-steroidal antiandrogens such as the imidazolidines, especially 1-(3'-trifluoromethyl-4'-nitrophenyl)-4,4-dimethyl-imidazoline-2,5-dione (also called Anandron) described in U.S. Pat. No. 4,097,578, or 4'-nitro-3'-trifluoromethylisobutyranilide (also called flutamide) described in U.S. Pat. No. 4,329,364 as well as the N-(phenylalkanoyl)aniline derivatives disclosed in U.S. Pat. No. 4,386,080 and the 3,4- disubstituted - branched - chain acylanilides disclosed in U.S. Pat. No. 4,239,776 (A. T. Glen et al.). Flutamide is the preferred antiandrogen.

Typical suitable steroidal antiandrogens include 6-chloro-1,2-dihydro-17-(acetyloxy)-3'H-cyclopropa[1,2]pregna-1,4,6-triene-3,20-dione, available under the tradename of Androcur from Schering A.G., W. Berlin, 17-(acetyloxy)-6-methyl-pregna-4,6-diene-3,20-diene, also called megestrol acetate and available from Mead Johnson & Co., Evansille, Ind. under the tradename of Megace.

Typical suitable antiestrogens include those steroidal and non-steroidal antiestrogens such as (1RS,2RS)-4,4'-diacetoxy-5,5'-difluoro-(1-ethyl-2-methylene)di-m-phenylenediacetate, which is available from Biorex under the tradename of Acefluranol, 6α-chloro-16α-methyl-pregn-4-ene-3,20-dione which is available from Eli Lilly & Co., Indianapolis, Ind. under the tradename of Clometherone, 6-chloro-17-hydroxypregna-1,4,6-triene-3,20-dione which is available as the acetate salt from Syntex Labs, Palo Alto, Cal. as Delmadione Acetate, 17-hydroxy-6-methyl-19-norpregna-4,6-diene-3,20-dione which is available from Theramex under the name of Lutenyl, 1-[2-[4-[1-(4-methoxyphenyl)-2-nitro-2-phenylethenyl]phenoxy]ethyl]-pyrrolidine which is available as the citrate salt from Parke-Davis Div. of Warner-Lambert Co., Morris Plains, N.J. under the name of Nitromifene Citrate, substituted aminoalkoxyphenylalkenes such as (Z)-2-[4-(1,2-diphenyl-1-butenyl)phenoxy]-N,N-dimethylethanamine which is available as the citrate salt from Stuart Pharmaceuticals, Wilmington, Del. as Tamoxifen Citrate (see also Belgian Pat. No. 637,389, Mar. 1964), 3,4-dihydro-2-(p-methoxyphenyl)-1-naphthyl p-[2-(1-pyrrolidinyl)ethoxy]phenyl ketone which is available as the methane sulfonate salt from Eli Lilly & Co. under the tradename of Trioxifene Mesylate, 1-[4'-(2-dimethylaminoethoxy)-phenyl)-1-(3'-hydroxyphenyl)-2-phenyl-but-1-ene, which is available from Klinge Pharma, 6-hydroxy-2-(p-hydroxyphenyl)-benzo(b)thien-3-yl[2-(1-pyrrolidinyl)-ethoxyphenyl]ketone which is available from Eli Lilly & Co. (LY-117018), [6-hydroxy-2-(4-hydroxyphenyl)benzo(b)thien-3-yl]-[4-(2-(1-piperdinyl)-ethoxy)phenyl]methanone, which is available from Eli Lilly & Co. as the hydrogen chloride salt (LY-156758) and meso-3,4-bis(3'-hydroxyphenyl)hexane as well as the dimethyl, dipropyl and 3'-acetoxyphenyl analogues which are described in U.S. Pat. No. 4,094,994 and a series of 1-phenyl-alkane and -alkenes, e.g. (E)-3-cyclopentyl-1-(4-hydroxyphenyl)-1-phenyl-1-butene and 2-cyclopentyl-1-[4-hydroxy- or methoxyphenyl]-3-phenyl-2-propen-1-ol and FC-1157 which is available as the citrate salt from Farmos Group, Ltd., Turku, Finland (see also Eur. Pat. Appln. No. EP 78,158). FC-1157, LY-117018, LY-156578 and Tamoxifen are the preferred antiestrogens. A pure antiestrogen is more preferred.

The inhibitors of sex steroid biosynthesis found useful in the present invention include those compounds which inhibit biosynthesis of sex steroids and precursor sex steroids of adrenal origin, preferably of ovarian and adrenal origin.

Thus, in another preferred aspect of the present invention, an inhibitor of sex steroid biosynthesis such as 3-(4-aminophenyl)-3-ethyl-2,6-piperidinedione which is commonly called aminoglutethimide, which is an inhibitor of sex steroid biosynthesis of adrenal but also ovarian origin and which is available from Ciba Pharmaceutical Co., Summit N.J. under tradename Cytadren, or ketoconazole which is available from Janssen Pharmaceutica, Piscataway, N.J. under the tradename Nizoral is administered in combination with the LH—RH agonist or antagonist, the antiandrogen and optionally the antiestrogen for treatment of breast cancer.

When an inhibitor of adrenal sex steroid biosynthesis, e.g., aminoglutethimide is administered, cortisol biosynthesis is blocked. Accordingly, hydrocortisone is administered in physiological amounts sufficient to maintain normal glucocorticoid levels.

In this invention, the association of the LH—RH agonist or antagonist, antiandrogen and the inhibitor of steroid biosynthesis and hydrocortisone and optionally antiestrogen are administered as pharmaceutical compositions via topical, parenteral or oral means. The LH—RH agonist or antagonist is administered parenterally, i.e., intramuscularly, subcutaneously or intravenously by injection or infusion by nasal drops or intravaginally by suppository. The LH—RH agonist or antagonist also may be microencapsulated in or attached to a biocompatable, biodegradable polymer, e.g., poly(d,l-lactide-coglycolide) and subcutaneously or intramuscularly injected by a technique called subcutaneous or intramuscular depot to provide continuous, slow release of the LH—RH agonist or antagonist over a period of 30 days or longer. The most preferred route of administration of the LH—RH agonist or antagonist is subcutaneous depot injection. Preferably the antiandrogen and antiestrogen (when used) will each be administered orally. Preferably the inhibitor of sex steroid biosynthesis, e.g. aminoglutethimide and/or ketoconazole are administered orally.

The amount of each component administered is determined by the attending clinicians taking into consideration the etiology and severity of the disease, the patient's condition and age, the potency of each component and other factors.

The LH—RH agonist or antagonist is generally administered at from about 10 to 5000 μg per day, with contemplated dosage ranges of about 10 to 1500 μg per day and about 200 to 500μ per day for the LH—RH agonist, and about 50–5000 μg per day for the LH—RH antagonist being preferred.

In the most preferred embodiment of this invention, the LH—RH agonist or antagonist is administered subcutaneously in a daily dose of about 500 μg for the first 30 days and thereafter subcutaneously in a daily dose of about 250 μg regardless of the patients' body weight. When the LH—RH agonist or antagonist is administered, once every 30-day period or even longer, by intramuscular or subcutaneous depot injection, a dose from about 300 to 150000 μg per 30-day period is used, with a dose of about 750 to 15000 μg per 30-day period being preferred.

The antiandrogen compositions are generally administered in a dosage range of about 0.20 to 40 mg/kg (body weight) per day with 750 mg per day in three equally divided doses being preferred.

The antiestrogen compositions (when used) are administered in a dosage range of about 0.1 to 10 mg/kg body weight per day, with 10 mg in two equally divided doses being preferred.

The aminoglutethimide compositions when used are administered initially in a dosage of about 250 mg given at 8-hour intervals and the dosage may be increased in increments of about 250 mg daily up to a total daily dose of about 2 grams.

The hydrocortisone compositions are administered orally in a dosage range of about 0.1 to 20 mg/kg body weight per day. Preferably, the hydrocortisone is administered orally at the dose of about 10 mg in the morning and about 5 mg doses in the afternoon and in the evening.

The ketoconazole compositions when used are administered orally in a dose of about 250 mg given at 8-hour intervals and may be increased to about 2 grams per day.

The LH—RH agonist or antagonist and antiandrogen and and inhibitor of sex steroid bisoynthesis and antiestrogen (when used) each may be administered separately or when the modes of administration are the same, all or two of them may be administered in the same composition, but in any case the preferred ratio of LH—RH agonist to antiandrogen to antiestrogen to inhibitor of sex steroid biosynthesis administered daily will be about 250 μg of LH—RH agonist to about 750 mg of antiandrogen to about 15 mg of antiestrogen to about 750 mg of sex steroid biosynthesis inhibitor.

In the most preferred aspect of this invention, the LH—RH agonist is [D-Trp$^6$,des-Gly NH$_2^{10}$]LH—RH ethylamide which is administered subcutaneously in single daily dose of about 500 μg for the first thirty (30) days of treatment and thereafter in a single daily dose of about 250 μg; the antiandrogen is 4'-nitro-3'-trifluoromethyl-isobutyranilide, i.e., flutamide, which is administered orally in three equally divided daily doses of about 250 mg; the inhibitor of sex steroid biosynthesis is ketoconazole or aminoglutethimide which is administered orally in three equally divided daily doses of about 250 mg; the hydrocortisone is administered orally at a dose of about 10 mg in the morning and two equally divided doses of about 5 mg, 8 and 16 hours thereafter. The antiestrogen, when used, is (Z)-2-[p-(1,2-diphenyl-1-butenyl)phenoxy]-N,N-dimethyl ethylamine (Tamoxifen) which is administered orally in three equally divided doses of about 10 mg every 12 hours.

The inhibitor of steroid biosynthesis and antiandrogen are preferably administered to a female in need of the breast cancer treatment of this invention one or two days before the LH—RH agonist or antagonist is administered, but the attending clinician may elect to start administration of the LH—RH agonist or antagonist, the antiandrogen and the inhibitor of sex steroid biosynthesis on the first day of the treatment.

When patients whose ovaries have already been removed are treated according to this invention, the antiandrogen and the inhibitor(s) of steriod biosynthesis such as aminoglutethimide and or ketoconazole administration and dosage are the same as indicated when the antiandrogen or the association of the antiandrogen and inhibitor(s) of sex steroid biosynthesis are used in combination with the LH—RH agonist or antagonist as well as the optional ingredient, the antiestrogen.

The LH—RH agonists or antagonists useful in the present invention are typically amorphous solids which are freely soluble in water or dilute acids, e.g., HCl, H$_2$SO$_4$, citric, acetic, mandelic or fumaric. The LH—RH agonist or antagonist for subcutaneous injection is supplied in vials containing 6 mL of sterile solution with the LH—RH agonist or antagonist at a concentration of about 1.0 mg/mL.

A typical pharmaceutical composition of the LH—RH agonist or antagonist include the LH—RH agonist or antagonist or a pharmaceutically acceptable acid salt thereof, benzyl alcohol, a phosphate buffer (pH=6.9–7.2) and sterile water.

The LH—RH agonist or antagonist for intramuscular or subcutaneous depot injection may be microencapsulated in a biocompatible, biodegradable polymer, e.g., poly (d,l-lactide-co-glycolide) by a phase separation process or formed into a pellet. The microspheres may then be suspended in a carrier to provide an injectable preparation or the depot may be injected in the form of a pellet. See also European Patent Application EPA No. 58,481 published Aug. 25, 1982 for solid compositions for subdermal injection or implantation or liquid formulations for intramuscular or subcutaneous injections; containing biocompatible, biodegradeable polymers such as lactide-glycolide copolymer and an LH—RH agonist, e.g., D-Ser-t-BuO$^6$, Azgly$^{10}$-LH—RH.

The aminoglutethimide and ketoconazole and hydrocortisone are typically compounded in customary ways for oral administration, e.g., in tablets, capsules and the like.

The antiandrogens useful in the present invention are typically formulated with conventional pharmaceutical excipients, e.g., spray dried lactose and magnesium stearate into tablets or capsules for oral administration. The antiestrogens, when used with the invention, are typically compounded in customary ways for oral administration, e.g., in capsules, tablets, as dragees or even in liquid form, e.g., suspensions or syrups. One or more of the active substances, with or without additional types of active agents, can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycols. Of course, taste-improving substances can be added in the case of oral-administration forms.

The therapeutically active antiestrogen compound should be present in a concentration of about 0.5–90% by weight of the total mixture, i.e., in amounts that are sufficient for maintaining the above-mentioned dosage range.

As further forms of administration, one can use plug capsules, e.g., of hard gelatin, as well as closed soft-gelatin capsules comprising a softener or plasticizer, e.g., glycerine. The plug capsules contain the active substance preferably in the form of a granulate, e.g., in mixture with fillers, such as lactose, saccharose, mannitol, starches, such as potato starch or amylopectin, cellulose derivatives or highly-dispersed silicic acids. In soft-gelatin capsules, the active substance is preferably dissolved or suspended in suitable liquids, such as vegetable oils or liquid polyethylene glycols.

In place of oral administration, all the active compounds may be administered parenterally. In such case, one can use a solution of the active substance, e.g., in sesame oil or olive oil.

Following the above treatment using the described regimen, breast tumor growth is inhibited and in some instances complete remission occurs.

What is claimed:

1. A method of treating breast cancer in a warm-blooded female animal in need of such treatment which comprises blocking the ovarian hormonal secretions of said animal by surgical or chemical means and in association therewith administering to said animal a therapeutically effective amount of an antiandrogen or pharmaceutical compositions thereof.

2. The method of claim 1 wherein the ovaries are surgically removed.

3. The method of claim 1 wherein the ovarian hormonal secretions are blocked by administering an amount of a LH—RH agonist or a LH—RH antagonist or a pharmaceutical composition thereof effective to block said hormonal secretions.

4. The method according to claim 1 wherein the LH—RH agonist is administered parenterally together with a pharmaceutically acceptable parenteral carrier.

5. The method of claim 1 wherein the antiandrogen is administered orally, together with a pharmaceutically acceptable oral carrier.

6. The method of claim 1 wherein the LH—RH agonist is a nonapeptide or a decapeptide represented by the formula: L-pyroglutamyl-L-histidyl-L-tryptophyl-L-seryl-L-tyrosyl-X-Y-L-arginyl-L-prolyl-Z, wherein X is D-tryptophyl, D-leucyl, D-alanyl, iminobenzyl-D-histyl, 3-(2-naphthyl)-D-alanyl, O-tert-butyl-D-seryl, D-tyrosyl, D-lysyl, D-phenylalanyl or N-methyl-D-alanyl and wherein Y is L-leucyl, D-leucyl, N$^\alpha$-methyl-D-leucyl, N$^\alpha$-methyl-L-leucyl or D-alanyl and wherein Z is glycyl-NHR$_1$ or NHR$_1$ wherein R$_1$ is H, lower alkyl or haloloweralkyl.

7. The method of claim 1 wherein the LH—RH agonist or LH—RH antagonist is administered as a subcutaneous depot injection.

8. The method of claim 1 wherein the antiandrogen is 1-(3'-trifluoromethyl-4'-nitrophenyl)-4,4-dimethylimidazoline-2,5-dione.

9. The method of claim 1 wherein the antiandrogen is 4'-nitro-3'-trifluoromethylisobutyranilide.

10. A method of treating breast cancer in a castrated warm-blooded female animal having breast cancer which comprises administering to said animal a therapeutically effective amount of an association of an antiandrogen and at least one inhibitor of sex steroid biosynthesis or pharmaceutical compositions thereof.

11. The method of claim 10 wherein the ovaries have been surgically removed.

12. The method of claim 10 wherein the ovarian hormonal secretions are blocked by administering an amount of a LH—RH agonist or a LH—RH antagonist or a pharmaceutical composition thereof effective to block said hormonal secretions.

13. The method of claim 10 which further comprises administering hydrocortisone or pharmaceutical compositions thereof.

14. The method of claim 10 wherein the antiandrogen and at least one inhibitor of sex steroid biosynthesis are each administered orally, together with a pharmaceutically acceptable oral carrier.

15. The method of claim 10 wherein the inhibitor of sex steroid biosynthesis is aminoglutethimide or a pharmaceutical composition thereof.

16. The method of claim 10 wherein the inhibitor of sex steroid biosynthesis is ketoconazole or a pharmaceutical composition thereof.

17. The method of claim 10 wherein the antiandrogen is 1-(3'-trifluoromethyl-4'-nitrophenyl)-4,4-dimethylimidazoline-2,5-dione.

18. The method of claim 10 wherein the antiandrogen is 4'-nitro-3'-trifluoromethylisobutyranilide.

19. A method of treating breast cancer in a warm-blooded female animal having breast cancer which comprises administering to said animal a therapeutically effective amount of an association of a LH—RH agonist or a LH—RH antagonist, an antiandrogen and at least one inhibitor of sex steroid biosynthesis or pharmaceutical compositions thereof.

20. The method of claim 19 wherein the LH—RH agonist is administered parenterally together with a pharmaceutically acceptable parenteral carrier.

21. The method of claim 19 wherein the inhibitor(s) of sex steroid biosynthesis and the antiandrogen are each administered orally, together with pharmaceutically acceptable oral carrier.

22. The method of claim 19 wherein the LH—RH agonist is administered at a daily parenteral dose of between about 250 and 500 μg.

23. The method of claim 19 wherein the antiandrogen is administered at a daily oral dose of between about 0.20 and 40 mg/kg and the inhibitor of steroid formation is administered at a daily oral dose of between about 0.20 and 40 mg/kg.

24. The method of claim 19 wherein one inhibitor of sex steroid biosynthesis or a pharmaceutical composition thereof is administered.

25. The method of claim 24 wherein the inhibitor of sex steroid biosynthesis is ketoconazole or a pharmaceutical composition thereof.

26. The method of claim 24 wherein the inhibitor of sex steroid biosynthesis is aminoglutethimide or a pharmaceutical composition thereof.

27. The method of claim 19 wherein two inhibitors of sex steroid biosynthesis or pharmaceutical composition thereof are administered.

28. The method of claim 27 wherein the two inhibitors of steorid biosynthesis are aminoglutethimide and ketoconazole or pharmaceutical compositions thereof.

29. The method of inhibiting the growth of breast tumors in a warm blood female animal whose ovarian hormonal secretions have been previously blocked by surgical or chemical means which comprises administering to the warm-blooded animal having such tumors a therapeutically effective amount of an association of an antiandrogen, hydrocortisone and an inhibitor of adrenal sex steroid biosynthesis, or pharmaceutical compositions thereof.

30. The method of claim 29 wherein the ovaries have been surgically removed.

31. The method of claim 29 wherein the ovarian hormonal secretions are blocked by administering an amount of a LH—RH agonist or a LH—RH antagonist or a pharmaceutical composition there of effective to block said hormonal secretions.

32. The method of claim 31 wherein the antiandrogen and an inhibitor of adrenal sex steroid biosynthesis are each administered orally together with a pharmaceutically acceptable oral carrier.

33. The method of claim 29 wherein the antiandrogen is 1-(3'-trifluoromethyl-4'-nitrophenyl)-4,4-dimethylimidazoline-2,5-dione.

34. The method of claim 29 wherein the antiandrogen is 4'-nitro-3'-trifluoromethylisobutyranilide.

* * * * *